United States Patent [19]

Sykes et al.

[11] 4,321,326

[45] Mar. 23, 1982

[54] PROCESS FOR PREPARING ANTIBIOTICS

[75] Inventors: Richard B. Sykes, Belle Mead; William L. Parker, Pennington, both of N.J.

[73] Assignee: E. R. Squibb & Sons, Inc., Princeton, N.J.

[21] Appl. No.: 238,288

[22] Filed: Feb. 25, 1981

[51] Int. Cl.$^3$ ............................................. C12P 17/10
[52] U.S. Cl. .................................... 435/121; 435/822; 260/239 A; 424/244
[58] Field of Search ......................................... 435/121

[56] References Cited

FOREIGN PATENT DOCUMENTS 21678 1/1981 European Pat. Off. .
55-7281379 12/1980 Japan .

OTHER PUBLICATIONS

Nature, 289:590 (1981).

*Primary Examiner*—Lionel M. Shapiro
*Attorney, Agent, or Firm*—Lawrence S. Levinson; Donald J. Barrack

[57] ABSTRACT

Culturing aerobically *Agrobacterium radiobacter* no. 31700 in a culture medium containing carbon and nitrogen sources yields the antibiotic substance EM5400, comprising salts of certain azetidinesulfonic acid derivatives.

2 Claims, No Drawings

PROCESS FOR PREPARING ANTIBIOTICS

RELATED APPLICATION

United States patent application Ser. No. 226,562, filed Jan. 19, 1981, discloses novel β-lactam antibiotics. These products are zwitterions or salts of a β-lactam having a sulfonic acid substituent —SO₃H in the 1-position and an acylamino substituent in the 3-position.

The application also discloses the biological production of (1) EM5117 (a salt of (R)-3-(acetylamino)-3-methoxy-2-oxo-1-azetidinesulfonic acid) by cultivation of Chromobacterium violaceum SC 11,378 and 2) EM5210 (a salt of (R)-3-[[N-(D-γ-glutamyl)-D-alanyl-]amino]-3-methoxy-2-oxo-1-azetidinesulfonic acid]) by cultivation of Gluconobacter species SC 11,435.

SUMMARY OF THE INVENTION

A mixture of antibiotic substances designated EM5400 is obtained by the novel process of this invention, which comprises cultivating a strain of the microorganism Agrobacterium radiobacter. The microorganism has been deposited in the American Type Culture Collection as A.T.C.C. 31700. The components of EM5400 have been isolated; they are salts of:

3-[[2-(acetylamino)-3-(4-hydroxyphenyl)-1-oxopropyl]amino]-3-methoxy-2-oxo-1-azetidinesulfonic acid (referred to herein as M53B2), 3-[[2-(acetylamino)-1-oxo-3-phenylpropyl]-amino]-3-methoxy-2-oxo-1-azetidinesulfonic acid (referred to herein as M53A2), 3-[[2-(acetylamino)-1-oxo-3-(sulfoxy)-3-[4-(sulfoxy)-phenyl]propyl]amino]-3-methoxy-2-oxo-1-azetidinesulfonic acid (referred to herein as M138),

[3S(R*)]-3-[[2-(acetylamino)-3-(4-hydroxyphenyl)-1-oxopropyl]amino]-2-oxo-1-azetidinesulfonic acid (referred to herein as M53B1), and 3-[[2-(acetylamino)-3-hydroxy-1-oxo-3-[4-(sulfoxy)-phenyl]propyl]amino]-3-methoxy-2-oxo-1-azetidinesulfonic acid (referred to herein as M101A).

DETAILED DESCRIPTION OF THE INVENTION

The Microorganism

The microorganism used for the production of EM5400 is a strain of Agrobacterium radiobacter isolated from the soil. A subculture of the organism may be obtained from the permanent collection of the American Type Culture Collection, Rockville, Md. Its accession number in this repository is A.T.C.C. No. 31700. In addition to the specific microorganism described and characterized herein, it should be understood that mutants of the microorganism (e.g., mutants produced through the use of x-rays, ultraviolet radiation or nitrogen mustards) can also be cultured to produce EM5400.

Agrobacterium radiobacter is a gram-negative rod that is motile by means of sub-polar to perithrichous flagella as evidenced by electron microscopy (negative staining with uranyl acetate).

Agrobacterium radiobacter is aerobic, growing optimally between 25° and 30° C.; no growth occurs at 41° C. The microorganism is cytochrome oxidase positive; it does not fluoresce on King's B medium; it does not grow on cetrimide-containing agar. Glucose is metabolized oxidatively by the microorganism. On Thornley's Medium 2A the microorganism is arginine dihydrolase negative. The microorganism produces copious amounts of extracellular polysaccharide slime on carbohydrate containing media (e.g., nutrient agar with 5% glucose or sucrose). 3-Ketolactose is produced from lactose. Congo red is taken up by the cells on congo-red mannitol agar.

No galls are produced on abraded stems of sunflower or tomato seedlings innoculated with a heavy suspension of Agrobacterium radiobacter.

The peritrichous flagella separate this organism from Pseudomonas and place it in the genus Agrobacterium. The production of 3-ketolactose separates it from Agrobacterium rhizogenes and Agrobacterium rubi. Failure to produce galls on test seedlings separates it from Agrobacterium tumefaciens placing it in Agrobacterium radiobacter, a saprophytic species.

The above characteristics conform with those of Agrobacterium radiobacter as cited in Bergey's Manual of Determinative Bacteriology, 8th Edition.

Fermentation of the Microorganism and Isolation of the Antibiotic

Agrobacterium radiobacter A.T.C.C. No. 31700 produces the antibiotic mixture EM5400. To form the antibiotic mixture EM5400 according to the preferred method, Agrobacterium radiobacter A.T.C.C. No. 31700 is grown at, or near, room temperature (25° C.) under submerged aerobic conditions in an aqueous nutrient medium containing an assimilable carbohydrate and nitrogen source. The fermentation is carried out for at least about 18 hours.

After the fermentation is completed, the beer is acidified, preferably to about pH 4, the cells removed by either centrifugation or filtration. The supernate is extracted with 0.05 M cetyldimethylbenzylammonium chloride in methylene dichloride, and the resulting extract, concentrated to a small volume, is then extracted with a 1.08 M aqueous solution of sodium thiocynate, at pH 4.35. The aqueous layer, reduced to a small volume, is diluted with 4 volumes of methanol to remove methanol insoluble impurities. The methanol soluble material is chromatographed on Sephadex G-10 with aqueous methanol (2:1, v/v). Progress of the fractionation in this and subsequent steps is followed by high voltage electrophoresis on pH 7 buffered paper. When applicable, thin layer chromatography on silica gel, with methylene dichloride:methanol (4:1, v/v) as developing solvent, is also done.

This Sephadex G-10 chromatographic procedure separates the bulk of the M53 components from M101A and M138. The M101A and M138 components are separated from each other by chromatography or Sephadex G-10 in water.

The crude M53 mixture (containing the M53A2, M53B1 and M53B2 components) is chromatographed on QAE Sephadex A-25 with a linear sodium nitrate gradient to separate M53A2 from a mixture of M53B1 and M53B2. Further purification of M53A2 is effected by trituration with methanol and chromatography on Diaion HP20AG resin to yield pure M53A2 as the sodium salt.

The M53B1-M53B2 mixture is desalted and partially resolved by chromatography on Diaion HP20AG resin. An enriched M53B1 fraction, so obtained, contaminated with M53B2, is converted into the potassium salt and purified by chromatography on Diaion HP20AG resin with water followed by water-methanol gradient. This gives pure M53B1 and a mixture of M53B1 and M53B2.

Fractions containing a mixture of M53B1 and M53B2 are combined and those components are converted to the tetrabutylammonium salts, which are then purified by chromatography on silicic acid. The M53B2 tetrabutylammonium salt is then converted to the potassium salt.

Crude M101A (from the Sephadex G-10 chromatography) is chromatographed on QAE Sephadex A-25 resin with a linear gradient of sodium nitrate, desalted, and successively chromatographed on Sephadex G-10 and Diaion HP20AG resins to yield the pure sodium salt.

Crude M138 (from the Sephadex G-10 chromatography) is subjected to chromatography on QAE Sephadex A-25 resin with a linear sodium nitrate gradient. Final purification is effected by Sephadex G-10 chromatography, yielding pure M138.

The compounds which make up the antibiotic mixture EM5400 can be used as agents to combate bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with these compounds. Such methods of administration include oral, intravenous, intramuscular, and as a suppository.

The following examples are specific embodiments of this invention.

EXAMPLE 1

Yeast beef agar slants are seeded with *Agrobacterium radiobacter* A.T.C.C., No. 31700, incubated for about 18 hours at 25° C., and used to inoculate 100 ml of medium composed of oatmeal (2%) and tomato paste (2%), contained in 500 ml Erlenmeyer flasks. The inoculated flasks are incubated at 25° C. for 24 hours on a rotary shaker, operating at 300 r.p.m. with a 2 inch throw.

A 1% (v/v) transfer is made from the germination flasks to Erlenmeyer flasks each containing 100 mL of fermentation medium. The composition of the fermentation medium is:

| Medium | Grams |
| --- | --- |
| Yeast extract | 5 |
| Glucose | 10 |
| Distilled water to 1,000 mL. | |

The medium is sterilized for 15 minutes at 121° C. and at 15 lbs. steam pressure prior to use. The inoculated fermentation flasks are incubated at 25° C. for 40 to 45 hours on a rotary shaker, operating at 300 r.p.m. with a 2 inch throw.

EXAMPLE 2

Fermentation

A 250 liter batch of *Agrobacterium radiobacter* A.T.C.C. No. 31700 is fermented in a 100 gallon stainless steel vessel with the media and operating conditions described below.

Stage 1

Inoculum: Culture of *Agrobacterium radiobacter* A.T.C.C. No. 31700 preserved by storing at −90° C. in 7% glycerol and grown out on agar slants of the following composition:

| Medium | Grams |
| --- | --- |
| Yeast extract | 1 |
| Beef extract | 1 |
| NZ Amine A | 2 |
| Glucose | 10 |
| Agar | 15 |
| Distilled water to 1,000 mL | |

The medium is adjusted to pH 7.3 and sterilized for 15 minutes at 121° C. and at 15 lbs. steam pressure prior to use.

A loopful of surface growth from the agar slant is used as the source of inoculum.

| Medium | Grams |
| --- | --- |
| Oatmeal | 20 |
| Tomato paste | 20 |
| Tap water to 1,000 mL | |

The pH of the medium is adjusted to pH 7.0 and sterilized for 15 minutes at 121° C. and at 15 lbs. steam pressure prior to use.

One hundred (100) ml of this medium, containing inoculum, in a 500 mL Erlenmeyer flask is incubated at 25° C. for about 24 hours on a rotary shaker. The shaker operates at 280 r.p.m. with a 2 inch throw.

Stage 2

Inoculum: 15 mL per flask from the first stage.
Medium: Same as Stage 1

Two 4-liter Erlenmeyer flasks, each containing 1.5 liters of inoculated medium, are incubated 24 hours on a rotary shaker. The shaker operates at 280 r.p.m. with a 2 inch throw.

Stage 3

Inoculum: 2,500 mL from Stage 2.
Medium: As described below

| Medium | Grams |
| --- | --- |
| Yeast extract | 5 |
| Glucose | 10 |
| Distilled water to 1,000 mL | |

Two hundred and fifty liters of the medium containing the inoculum is incubated for about 42 hours at 25° C. in a 100 gallon stainless steel fermentation vessel. During incubation, the broth is agitated at 155 r.p.m. and aereated at the rate of 10.0 cubic feet per minute. An antifoam agent (Ucon LB625, Union Carbide) is added as needed.

Isolation

The fermentation beer is adjusted to pH 4 with aqueous HCl and the cells separated by centrifugation. The supernate (200 L) is extrated with 40 L of 0.05 M cetyldimethylbenzylammonium chloride in dichloromethane and the extract concentrated in vacuo to 5.5 L. The concentrate is then extracted with a solution of 177 g of sodium thiocyanate in 2 L of water, adjusting the mixture of pH 4.35 with phosphoric acid. The organic phase is extracted with two additional portions of 0.72 M sodium thiocyanate. The combined aqueous extract is concentrated to 465 mL in vacuo and added to 1840 mL of methanol. Solids are filtered out and discarded. The filtrate is concentrated in vacuo and the residue triturated with 1250 mL of methanol. Solids are filtered out and discarded. The filtrate is concentrated in vacuo, giving 194 g of solid.

The solid is dissolved in 100 mL of methanol-water, 1:1, and chromatographed on a 5×106.5-cm (2.1 L) column of Sephadex G-10 packed in methanol-water, 2:1, eluting with this mixture at 2.85 mL/minute and collecting 20-mL fractions. Fractions 93-113, (containing M53) are combined, concentrated in vacuo, and methanol-insoluble material is removed, giving 3.37 g of residue A. Fractions 114-200 (containing M53, M101, M138 and NaSCN) are combined and concentrated in vacuo, giving 135 g of residue. This is triturated with 135 mL of methanol at 0°-5° C. and the soluble portion is concentrated in vacuo, giving 58 g of residue. This is chromatographed on a 5×108-cm column (2.1 L) of Sephadex G-10 in water at 2.85 mL/minute, collecting 20 mL fractions. Fractions are combined and concentrated to residues as follows: 54-68 (M138, residue B), 69-73 (M138 and M101, residue C), 74-78 (M101, residue D), 79-83 (M101 and M53, residue E), 84-93 (M53, residue F), 94-104 (sodium thiocyanate and trace of M53). Residues C and E are combined (1.3 g total) and rechromatographed on Sephadex G10 in water as above. Fractions 56-63 are combined with residue B and concentrated in vacuo, giving 5.76 g of crude M138. Fractions 64-83 are combined with residue D and concentrated, giving 1.43 g of crude M101. Fractions 84-101 are combined with residues A and F, and concentrated in vacuo, giving 3.5 g of crude M53.

Crude M53 is chromatographed on a 2.5×55-cm column (270 mL) of QAE Sephadex A-25 ($NO_3^-$ form), eluting at 3.33 mL per minute with a linear gradient prepared from 2.5 L of water and 2.5 L of 0.25 M sodium nitrates and collecting 20 mL fractions. Fractions 135-154 are combined and concentrated in vacuo, giving residue H (M53A and sodium nitrate). Fractions 155-181 similarly give residue I (M53B and sodium nitrate).

Residue H is triturated with methanol and the soluble fraction, 0.40 g, chromatographed on a 2.5×20-cm column of Diaion HP20AG, eluting at 2 mL per minute with water and collecting 20 mL fractions. Fractions 5-8 contain residual sodium nitrate. Fractions 12-25 are combined and concentrated, giving 9.6 mg of impure M53A1 (not further characterized). Fractions 26-75 similarly give 51.9 mg of M53A2 (sodium salt).

Residue I is partially desalted by trituration with methanol. The soluble fraction, 0.85 g, is chromatographed on Diaion HP20AG as described above. Fractions 11-18 are combined and concentrated, giving 202 mg of residue J (mostly M53B1 with some M53B2). Fractions 19-40 similarly give 23 mg of residue K (mixture of M53B1 and M53B2).

Residue J is converted to the potassium salt on a 1.1×10-cm column of Dowex 50W-X2 ($K^+$ form). The resulting potassium salt is chromatographed on a 2.5×54-cm column (265 mL) of Diaion HP20AG, eluting at 2 mL per minute with 1500 mL of water and then at 5 mL/minute with a linear gradient prepared from 500 mL of water and 500 mL of methanol-water, 1:1, and collecting 20 mL fractions. Fractions 30-40 are combined and concentrated, giving 106 mg of the potassium salt of M53B1. Fractions 41-100, containing mixed M53B1 and M53B2, are combined with residue K and concentrated, giving 86 mg of residue L.

Residue L is mixed with 84 mL of 0.5 M aqueous tetrabutylammonium sodium sulfate and the solution taken to dryness in vacuo. The residue is triturated with dichloromethane and the soluble portion concentrated, giving 222 mg of the tetrabutylammonium salt of mixed M53B1 and M53B2. This is chromatographed on a 120 mL column of Mallinckrodt SilicAR CC-4 packed in dichloromethane, eluting with methanol-dichloromethane in ratios of 1:19, 1:9, 1:4 and 2:3. Fractions containing M53B2 (detected by thin-layer chromatography on silica gel eluting with dichloromethane-methanol, 4:1) are combined and concentrated, giving 105 mg of M53B2, tetrabutylammonium salt. This is converted to the potassium salt on a 6 mL column of Dowex 50W-X2 (potassium form), giving 53 mg of M53B2, potassium salt, (contaminated with some inorganic material). Fractions containing M53B1 similarly give an additional 42 mg of the potassium salt of M53B1.

Crude M101, 1.43 g is chromatographed on a 2.5×24-cm (120 mL) column of QAE Sephadex ($NO_3^-$), eluting at 2 mL per minute with a linear gradient prepared from 1100 mL of water and 1 L of 1 M sodium nitrate, and collecting 20 mL fractions. Fractions 61-75 are combined, concentrated, and partially desalted by trituration with methanol. The soluble fraction is chromatographed on a 5×107-cm (2.1 L) column of Sephadex G-10, eluting at 2 mL per minute with water and collecting 20 mL fractions. Fractions 54-62 are combined and concentrated, giving 364 mg of crude M101A. Fractions 63-67 contain M101B (not further characterized), M101A and sodium nitrate. Crude M101A is chromatographed on a 5×56-cm (1.1 L) column of Diaion HP20AG, eluting with water at 2 mL/minute, and collecting 10 mL fractions. Fractions 91-103 are combined and concentrated, giving 135 mg of M101A, sodium salt.

Crude M138, 5.76 g, is chromatographed on a 2.5×27-cm (130 mL) column of QAE Sephadex A-25, eluting at 2 mL/minute with a linear gradient prepared from 2 L of water and 2 L of 2 M sodium nitrate and collecting 20 mL fractions. Fractions 71-101 are combined, concentrated, and partially desalted by trituration with methanol. The methanol-soluble material (7.55 g) is chromatographed on a 5×107-cm (2.1 L) column of Sephadex G-10, eluting at 2.5 mL per minute with water and collecting 20 mL fractions. Fractions 53-63 are combined and concentrated, giving 2.54 g of M138, sodium salt.

The materials referred to above by tradename are described below:

Sephadex G-10: cross-linked dextran gel (Pharmacia Fine Chemicals Inc.)

QAE Sephadex A-25: cross-linked dextran gel with diethyl-(2-hydroxypropyl)aminoethyl groups attached (Pharmacia Fine Chemicals Inc.).

Diaion HP20AG: Macroporous styrene-divinylbenzene copolymer (Mitsubishi Chemical Industries).

Dowex 50W-X2: Styrene-divinylbenzene copolymer with sulfo groups attached (Dow Chemical Co.).

SilicAR CC-4: Silicic-acid based adsorbent (Mallinckrodt, Inc.).

What is claimed is:

1. A process for the preparation of the antibiotic substance EM5400 which comprises culturing aerobically *Agrobacterium radiobacter* A.T.C.C. No. 31700 in a culture medium containing carbon and nitrogen sources until EM5400 is accumulated, and then recovering the EM5400 from the medium.

2. A process in accordance with claim 1 wherein the culturing is carried out at about 25° C.

* * * * *